(12) United States Patent
Kishi et al.

(10) Patent No.: US 10,981,806 B2
(45) Date of Patent: Apr. 20, 2021

(54) STERILIZER, SUPPLY DEVICE, AND STERILIZATION METHOD

(71) Applicant: ASAHI KASEI KABUSHIKI KAISHA, Tokyo (JP)

(72) Inventors: Hiroyuki Kishi, Tokyo (JP); Sho Sugiyama, Tokyo (JP); Shinji Miya, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 34 days.

(21) Appl. No.: 16/018,551

(22) Filed: Jun. 26, 2018

(65) Prior Publication Data

US 2018/0370821 A1   Dec. 27, 2018

(30) Foreign Application Priority Data

Jun. 27, 2017 (JP) .............................. JP2017-125188

(51) Int. Cl.
| | |
|---|---|
| *C02F 1/32* | (2006.01) |
| *A61L 2/10* | (2006.01) |
| *C02F 1/28* | (2006.01) |
| *C02F 1/22* | (2006.01) |

(52) U.S. Cl.
CPC .................. *C02F 1/32* (2013.01); *A61L 2/10* (2013.01); *C02F 1/22* (2013.01); *C02F 1/28* (2013.01); *C02F 1/325* (2013.01); *A61L 2202/11* (2013.01); *A61L 2202/23* (2013.01); *C02F 2201/3222* (2013.01); *C02F 2201/3228* (2013.01)

(58) Field of Classification Search
CPC .... C02F 1/325; C02F 1/32; C02F 2201/3228; C02F 2201/3222; C02F 2307/06; C02F 2303/04; A61L 2/10; A61L 2202/11
See application file for complete search history.

(56) References Cited

U.S. PATENT DOCUMENTS

| | | | |
|---|---|---|---|
| 4,899,057 A * | 2/1990 | Koji .......................... | A61L 2/08 250/436 |
| 7,683,344 B2 * | 3/2010 | Tribelsky .................. | A61L 2/10 250/428 |
| 2010/0178201 A1 | 7/2010 | Tribelsky et al. | |

(Continued)

FOREIGN PATENT DOCUMENTS

| | | |
|---|---|---|
| JP | 2007-502200 A | 2/2007 |
| JP | 5187577 B2 | 4/2013 |

(Continued)

*Primary Examiner* — Lessanework Seifu
(74) *Attorney, Agent, or Firm* — Morgan, Lewis & Bockius LLP

(57) ABSTRACT

To provide a sterilizer preventing ultraviolet ray absorption in a body of a case body and emitting ultraviolet rays to a portion to be sterilized without involving positioning with high accuracy. A sterilizer 1a has a case body 2 containing a member having an ultraviolet-ray transmission property and a flow passage formed thereinside and an ultraviolet-ray irradiation portion 3 irradiating a predetermined portion of a member configuring the case body 2 with ultraviolet rays, in which ultraviolet rays emitted from the ultraviolet-ray irradiation portion 3 travel in a body of the case body 2 to be radiated at least from an end surface on an output end side of the case body 2.

19 Claims, 11 Drawing Sheets

(56) References Cited

U.S. PATENT DOCUMENTS

| | | |
|---|---|---|
| 2016/0046508 A1 | 2/2016 | Orita |
| 2018/0099061 A1* | 4/2018 | Asano .................. A61L 2/10 |
| 2018/0208486 A1 | 7/2018 | Konagayoshi et al. |
| 2019/0047877 A1* | 2/2019 | Geboers .................. C02F 1/325 |

FOREIGN PATENT DOCUMENTS

| | | |
|---|---|---|
| JP | 2014-076205 A | 5/2014 |
| JP | 2014-189299 A | 10/2014 |
| JP | 2016-190215 A | 11/2016 |
| JP | 2017060668 A | 3/2017 |
| JP | 2018-061618 A | 4/2018 |

* cited by examiner

STERILIZER, SUPPLY DEVICE, AND STERILIZATION METHOD

BACKGROUND OF THE INVENTION

Field of the Invention

The present invention relates to a sterilizer, a supply device supply including the sterilizer, and a sterilization method.

Description of the Related Art

In recent years, there are water supply devices, such as a water server configured to store drinking water, such as RO (Reverse Osmosis) water or mineral water, in a water storage tank and supply the stored drinking water by a user's cock operation or button operation for drinking. In water storage portions of the water supply devices, a mechanism of cooling or heating water to enable easy supply of cold water or hot water is added in many cases.

In such water supply devices, a mechanism of suppressing the development and proliferation of bacteria, i.e., a sterilization mechanism, has been introduced in many cases. In the example of the water server, the water itself delivered with a bottle is basically sterilized, and therefore the sterilization is performed for the purpose of preventing the bottled water from being contaminated by bacteria within the water server after placing the bottle in the water server. As a method for performing the sterilization, a method is mentioned which periodically circulates hot water through pipes inside the water supply devices, such as the water server, to thereby sterilize bacteria staying in the pipes to be mixed in bottled water. Moreover, the water supply devices have been devised, e.g., fixing an introduction port of air entering for filling the capacity corresponding to the supply capacity in supplying water from the water supply device, and then installing a fine filter therein to prevent bacteria from entering the water supply device from the air, providing a mercury lamp in a cold-water tank to perform sterilization by ultraviolet-ray irradiation, or combining the methods described above to enhance the bactericidal effect. These methods are devices of the sterilization performed for preventing the proliferation of bacteria introduced into water flow passages of the water supply device with the air from the outside within the water supply device.

However, a water outlet is mentioned as a portion which needs to be particularly focused as a portion where bacteria are frequently generated which can be seen in common in the water supply devices, such as the water server, slightly independent of the generation of bacteria and the mechanism for sterilization thereof described above. In the water outlet, bacteria are likely to be generated because drinking water touches air when water is supplied, drinking water rebounding when water is supplied is deposited to the water outlet, or a liquid pool arises in the water outlet. Therefore, the water outlet is likely to become insanitary and the bacteria are easily mixed into supplied water (drinking water), and therefore the water outlet needs to be cleaned at a high frequency to make the water outlet sanitary for drinking.

In order to reduce the cleaning frequency, a method has been proposed which includes partially coating the water outlet with a photocatalyst, and then irradiating the portion coated with the photocatalyst with ultraviolet rays to thereby sterilize the water outlet by the strong oxidation capacity of the photocatalyst excited by the ultraviolet rays and the sterilization capacity of the ultraviolet rays, for example (for example, refer to Patent Document 1). Moreover, a method has also been proposed which includes determining a flow passage in which flowing water is irradiated with ultraviolet rays required for sterilization and the ultraviolet-ray irradiation direction on the same line in the water outlet, and then emitting ultraviolet rays from the ultraviolet-ray irradiation direction to thereby sterilize the flowing water passing through the water outlet and sterilize the inner wall surface configuring the water outlet (for example, refer to Patent Document 2).

CITATION LIST

Patent Literature

PTL 1: JP 2014-189299 A
PTL 2: Japanese Patent No. 5187577

SUMMARY OF THE INVENTION

However, in the method described in Patent Document 2, for example, ultraviolet rays need to be emitted in the straight direction towards a portion to be sterilized, and therefore there is a necessity of positioning the light source of the ultraviolet rays and the portion to be sterilized with sufficient accuracy. Therefore, there is a problem that the arrangement positional relationship therebetween causes limitations of the shape design of the water supply device or an increase in the size of the water supply device, e.g., a water outlet portion is not curved to be easily irradiated with light, a large number of light sources need to be disposed to be able to irradiate the entire region contacting water of the water outlet portion, and the like. Moreover, the method described in Patent Document 1 is configured so that the water outlet is irradiated with ultraviolet rays, whereby the ultraviolet rays are diffused into a water outlet body to reach the inner peripheral surface configuring the flow passage of the water outlet while repeatedly reflecting to be further diffused to a water outlet end portion. However, in this case, the amount of the ultraviolet rays reaching a portion to be sterilized has not been sufficient because the ultraviolet rays are absorbed by a member configuring the water outlet body or the ultraviolet rays are reflected on the interface between air and the water outlet body. Or, in order to achieve a sufficient amount of ultraviolet rays in sterilizing, the light source itself needs to be made more powerful but an increase in the output of the light source presents a new problem in terms of design of inducing consideration to a degradation or the like of a water supply device constituent member by the ultraviolet rays.

The present invention has been made focusing on the above-described former unsolved problems. It is an object of the present invention to provide a sterilizer preventing ultraviolet ray absorption near a discharge port of drinking water or the like and capable of more effectively emitting ultraviolet rays to a portion to be sterilized without involving the above-described design limitations caused by the positioning with an ultraviolet-ray light source, and further a device for supplying drinking water or the like having the sterilizer and a sterilization method.

In order to achieve the object, a sterilizer according to one aspect of the present invention includes a case body composed of a member having an ultraviolet-ray transmission property and including a discharge passage formed thereinside and a light source irradiating a predetermined portion of the member with ultraviolet rays, in which the ultraviolet rays emitted from the light source travel in a body of the case body and the ultraviolet rays are radiated at least from an end surface on the side of a discharge port of the case body. The predetermined portion herein refers to a position other than the end surface on the discharge port side of the case body.

A device for supplying a liquid or a solid according to another aspect of the present invention has the sterilizer according to the above-described aspect in a supply port and supplies liquid or a solid obtained by freezing liquid.

Furthermore, a sterilization method according to another aspect of the present invention includes disposing the sterilizer according to the above-described aspect in a supply port of a device for supplying liquid or a solid obtained by freezing liquid and preventing the propagation of bacteria in the supply port by covering the supply port with the sterilizer.

The present invention enables effective light gathering to the end surface of the discharge port by emitting the ultraviolet rays to the body of the case body instead of directly emitting the ultraviolet rays to a body to be irradiated in the case body having the discharge port of drinking water or the like and enables sterilization by the supply of sufficient ultraviolet rays to a portion to be sterilized. Moreover, simultaneously therewith, limitation about the arrangement position of the ultraviolet-ray light source near the discharge port decreases, and therefore a smaller sterilizer with high degree of freedom in designing can be configured. Furthermore, an excellent device for supplying a liquid or solid and an excellent sterilization method for drinking water or the like using the same can be provided.

The present invention also provides not only the water server but an effective sterilization method for portions of general outlets of supplies in devices for supplying water, drinks, or ice.

DESCRIPTION OF THE PREFERRED EMBODIMENTS

Figure 1A:
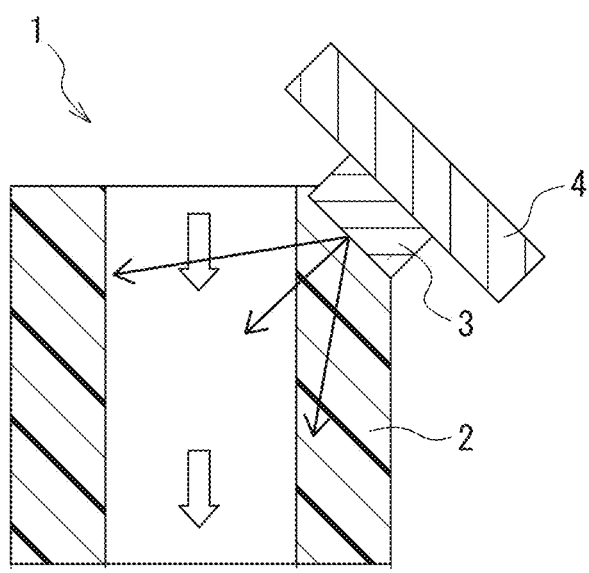
FIGS. 1A and 1B are schematic configuration diagrams illustrating an example of a sterilizer according to one embodiment of the present invention.

Next, one embodiment of the present invention is described with reference to the drawings. In the following description of the drawings, the same or similar portions are designated by the same or similar reference numerals. However, it should be noted that the drawings are schematically illustrated and the relationship between the thickness and the plane dimension and the ratio of the thickness of each layer are different from the actual relationship and ratio. Therefore, a specific thickness or dimension should be determined considering the following description. Moreover, it is a matter of course that portions where the mutual relationships or the ratios of dimensions are different from each other between the drawings are included.

Moreover, the embodiments described below describe examples of a device or a method for crystalizing the technical idea of the present invention and the technical idea of the present invention does not specify materials, shapes, structures, arrangement, and the like of constituent components to those described below. The technical idea of the present invention can be variously altered in the technical scope specified by Claims.

Figure 1B:
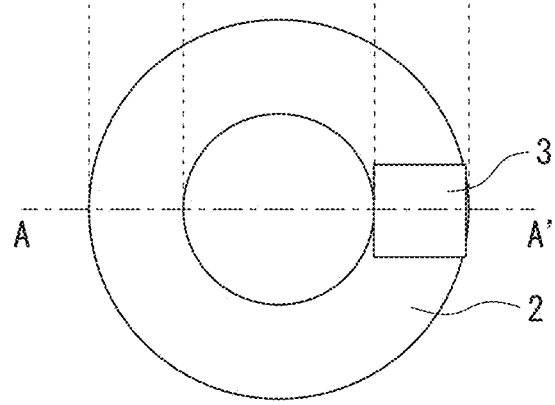

FIGS. 1A and 1B are schematic views illustrating an example of a sterilizer according to one embodiment of the present invention. FIG. 1A is a cross-sectional view of the A-A' line of FIG. 1B and FIG. 1B is a plan view. In FIG. 1B, a printed circuit board (PCB) 4 described later is omitted. A sterilizer 1 is provided in a supply port end portion of a device supplying drinking water, ice, and the like, such as a water server, whereby the supply port end portion is maintained in a sterilized state and an output end of the sterilizer 1 is maintained in the sterilized state.

As illustrated in FIGS. 1A and 1B, the sterilizer 1 has a case body 2 having a hollow columnar shape, an ultraviolet-ray irradiation portion (light source) 3 irradiating a member body forming the case body 2 (hereinafter also referred to as a body of the case body 2) with ultraviolet rays, and the printed circuit board 4 on which the ultraviolet-ray irradiation portion 3 is mounted. FIGS. 1A and 1B illustrate a case where the case body 2 is a column.

The case body 2 has translucency to ultraviolet rays and contains a material having a characteristic that the optical refractive index to ultraviolet rays is relatively high. The hollow portion of the case body 2 configures the flow passage (discharge passage). One end of the case body 2 serves as an output end (discharge port) of liquid or the like passing through the flow passage and the other end serves as an attachment end attached to the supply port of the device for supplying a liquid or a solid.

The product of the maximum distance (cm) from the ultraviolet-ray irradiation portion 3 and the absorption coefficient ($cm^{-1}$) using a common logarithm with base 10 of the case body 2 is preferably less than 3, more preferably less than 2, and still more preferably less than 1.5. This is because the amount of ultraviolet rays lost in the body of the case body 2 is small in the range above.

Materials of the case body 2 are preferably materials transmitting 30%/cm or more of ultraviolet rays with a center wavelength of 230 nm or more and 300 nm or less. The case body 2 is composed of silicone resin or quartz, for example. In the range above, the amount of ultraviolet rays lost in the body of the case body 2 decreases. The materials of the case body 2 are preferably those containing at least one of crystal, quartz, silicone resin, fluororesin, and polyolefin. The polyolefin is preferably polycycloolefin, polymethylpentene, or the like from the viewpoint of the ultraviolet-ray transmission property. Moreover, by appropriately adjusting additives, such as antioxidants and ultraviolet-ray resistant additives, polyethylene, polypropylene, and polyolefin resins containing derivatives thereof are usable.

The case body 2 may be partially covered with an ultraviolet-ray reflecting substance. The ultraviolet-ray reflecting substance refers to a material with a reflectance at a wavelength to be used for sterilization of more than 30%. As the ultraviolet-ray reflecting substance, at least one of aluminum, gold, silver, copper, and platinum group elements including platinum, or an alloy containing the same can be mentioned. By covering the case body 2 with the ultraviolet-ray reflecting substance, the ultraviolet irradiation intensity to the inside of the body of the case body 2 can be improved or the amount of ultraviolet rays in the circumferential environment can be adjusted. In order to reduce the leakage of ultraviolet rays to the outside of the case body 2, the case body 2 may be covered with a resin material absorbing ultraviolet rays.

The ultraviolet-ray irradiation portion 3 is composed of a diode emitting ultraviolet rays with a center wavelength of 230 nm or more and 300 nm or less, for example. The ultraviolet-ray irradiation portion 3 is disposed on the end surface on the attachment end side of the case body 2. At this time, the ultraviolet-ray irradiation portion 3 is disposed in such a manner that ultraviolet rays emitted from the ultraviolet-ray irradiation portion 3 are diffused into the body of the case body 2 to be radiated from the entire end surface on the side of an output end of the case body 2. Specifically, the ultraviolet-ray irradiation portion 3 is disposed to be inclined on a corner portion of the case body 2 as viewed from the side surface in such a manner that the light emission surface of the ultraviolet-ray irradiation portion 3 and the direction where the case body 2 extends cross each other. Thus, ultraviolet rays are emitted to a body to be irradiated deposited to the end surface on the output end side of the case body 2. In other words, the body to be irradiated deposited to the end surface on the output end side of the case body 2 can be sterilized.

The ultraviolet-ray irradiation portion 3 is not limited to the ultraviolet-ray emitting diode.

The ultraviolet-ray irradiation portion 3 may be provided at the other positions insofar as the position does not include the end surface on the output end side of the case body 2. Thus, by providing the ultraviolet-ray irradiation portion 3 at a position different from the end surface on the output end side of the case body 2, ultraviolet rays emitted from the ultraviolet-ray irradiation portion 3 can be radiated from the end surface on the output end side while being diffused in the body of the case body 2, and thus the body to be irradiated deposited to the end surface on the output end side can be easily sterilized.

On the printed circuit board 4, the ultraviolet-ray irradiation portion 3 is mounted and a control circuit controlling the irradiation timing by the ultraviolet-ray irradiation portion 3 and the like which are not illustrated are mounted, for example.

Next, an operation of the sterilizer 1 is described.

When the ultraviolet-ray irradiation portion 3 is driven in a state where drinking water or the like is not supplied from the water supply device to which the sterilizer 1 is attached, the irradiation light emitted from the ultraviolet-ray irradiation portion 3 is diffused into the body of the case body 2.

Figure 2A:
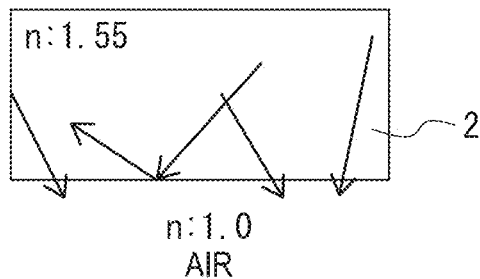
FIGS. 2A and 2B are explanatory views for explaining an operation of the sterilizer.
Figure 2B:
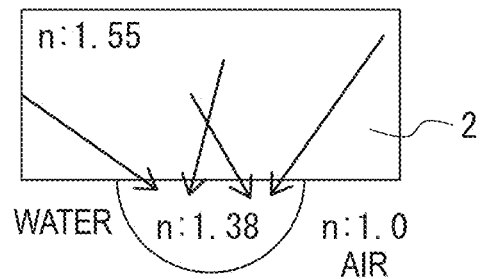

Herein, the case body 2 has a characteristic that the optical refractive index to ultraviolet rays is high, and therefore, most of the ultraviolet rays emitted to the body of the case body 2 is totally reflected on the wall surface of the case body 2 as illustrated in FIG. 2A. However, when water to be supplied from the water supply device is deposited to the wall surface, for example, as illustrated in FIG. 2B, the optical refractive index (n=1.36) to the ultraviolet rays of the water is higher than the optical refractive index (n=1.0) to the ultraviolet rays of air. When the case body 2 is composed of quartz, for example, the optical refractive index n to the ultraviolet rays of the case body 2 is n=1.5, and thus a difference in the optical refractive index to the ultraviolet rays between the case body 2 and the water is relatively small. As a result, in the region where the water is deposited, the totally reflecting ultraviolet rays decrease and ultraviolet rays transmitting the boundary surface between the case body 2 and the water to be radiated to the outside of the case body 2 increase. More specifically, the case body 2 preferably contains a material which reduces the difference in the optical refractive-index.

Examples of materials with low refractive indices include amorphous fluororesin of n=1.29. When the optical refractive index to ultraviolet rays of a light emission portion of the ultraviolet-ray irradiation portion 3 (light source) is set to Nd, the optical refractive index of the case body 2 is preferably 1.29 or more and the Nd or less. More preferably, when the Nd is $1.36 \leq Nd$, 1.29 or more and "$1.36-0.5 \times (Nd-1.36)$" or more and "$1.36+0.5 \times (Nd-1.36)$" or less. In the case of $1.36 > Nd$, the optical refractive index of the case body 2 is preferably 1.29 or more and "$1.36+0.5 \times (Nd-1.36)$" or more and "$1.36-0.5 \times (Nd-1.36)$" or less.

By forming the case body 2 with materials having such optical reflective indices, when the water to be supplied from the water supply device is deposited to the end surface on the output end side of the case body 2 or a region on the output end side of the outer peripheral surface, for example, ultraviolet rays are hard to be totally reflected and are likely to transmit the boundary surface between the case body 2 and the water to be radiated to the outside of the case body in the region where the water is deposited. More specifically, ultraviolet rays are emitted to the water deposited to the case body 2, and thus sterilization is performed. Then, a large number of ultraviolet rays are totally reflected in a region where no water is deposited to the case body 2, and therefore the ultraviolet rays are hard to be radiated to the outside of the case body 2. More specifically, ultraviolet rays are likely to be radiated to the outside of the case body 2 only in a region to be irradiated with the ultraviolet rays, and sterilization is performed and ultraviolet rays are hard to be radiated to the outside of the case body 2 in a region not to be irradiated with ultraviolet rays. Therefore, the radiation of unnecessary ultraviolet rays to the outside of the case body 2 can be suppressed, and sufficient ultraviolet rays can be correspondingly emitted to the region to be irradiated with ultraviolet rays.

Thus, the sterilizer 1 according to one embodiment of the present invention can selectively condense ultraviolet rays to the region where the water is deposited utilizing a difference in the optical refractive index to the ultraviolet rays between the water and air to the optical refractive index to the ultraviolet rays of the case body 2. More specifically, ultraviolet rays can be selectively condensed to the region where the water is deposited, i.e., the portion to be sterilized, and therefore the portion can be efficiently sterilized.

Moreover, the ultraviolet-ray irradiation portion 3 is provided in the end portion on the attachment end side of the case body 2, and therefore ultraviolet rays travel while repeatedly reflecting in the body of the case body 2 from the end portion on the attachment end side of the case body 2 to the end portion on the output end side. Therefore, due to the fact that ultraviolet rays travel while repeatedly reflecting in the body of the case body 2, ultraviolet rays can be emitted to water droplets or the like deposited to the outer periphery of the case body 2, and thus the entire outer periphery of the case body 2 can be sterilized.

When drinking water or the like is supplied from the water supply device to which the sterilizer 1 is attached, the drinking water or the like is difficult to be deposited to the end surface on the output end side of the case body 2. Even when deposited thereto, drinking water or the like is continuously discharged, and therefore bacteria are difficult to propagate in the state where the drinking water or the like is supplied. Moreover, drinking water or the like stored in the water supply device is usually sterilized by a separately provided sterilization device or the like, and therefore, when drinking water or the like is supplied, the sterilizer 1 may not be operated. On the contrary, when drinking water or the like is not supplied from the water supply device, the drinking water or the like deposited to the end surface on the output end side of the case body 2 or the surrounding thereof remains deposited thereto, and therefore bacteria are likely to propagate. Therefore, when drinking water or the like is supplied from the water supply device, the sterilizer 1 is not operated and, only when drinking water or the like is not supplied, the sterilizer 1 is operated, whereby the sterilizer 1 can be operated only when required, and thus the power required for the drive of the sterilizer 1 can be correspondingly reduced. When drinking water or the like is not supplied from the water supply device, the sterilizer 1 may not be always driven and the sterilizer 1 may be operated periodically or at predetermined timing, e.g., timing when predetermined time has passed from the timing when the supply of drinking water or the like from the water supply device is stopped.

Similarly on the inner peripheral surface of the case body 2, when water is deposited thereto, ultraviolet rays are likely to be radiated to the outside of the case body 2 and, on the contrary, when water is not deposited thereto, ultraviolet rays are hard to be radiated to the outside of the case body 2. Even in a case where ultraviolet rays are radiated to the outside of the case body 2 on the inner peripheral surface, when the radiated ultraviolet rays are made incident into the region to which water is deposited of the inner peripheral surface, the radiated ultraviolet rays travel into the body of the case body 2 again to be confined in the body of the case body 2. Therefore, a reduction in the ultraviolet rays traveling in the body of the case body 2 due to the ultraviolet rays being radiated to the outside of the case body 2 on the inner peripheral surface can be suppressed.

Figure 3A:
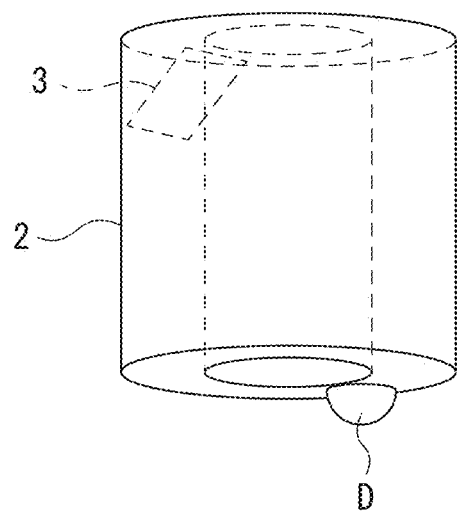
FIGS. 3A to 3D are examples of simulation results illustrating the travel of light.
Figure 3B:
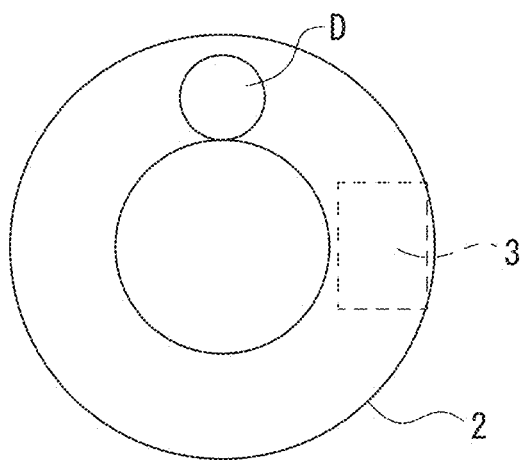
Figure 3C:
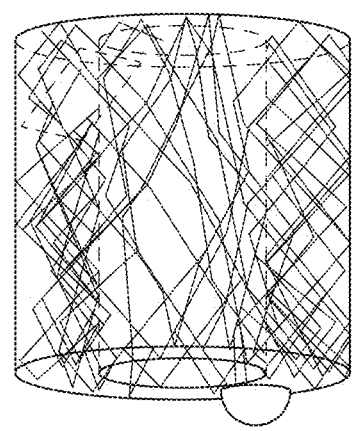
Figure 3D:
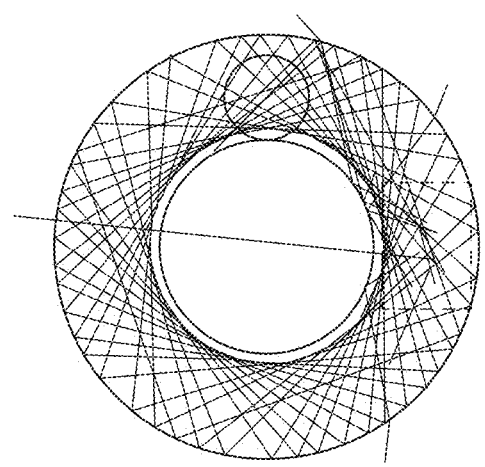

Herein, a simulation when the case body 2 is irradiated using one having an outer diameter ϕ of 10 mm, an inner diameter ϕ of 5 mm, and a height of 10 mm as the case body 2 and using a 3.5 mm square surface light source which is an ultraviolet-ray emitting diode having a 20 mW output as the ultraviolet-ray irradiation portion 3 was performed. The simulation was performed supposing a case where a water droplet D having a 1 mm in radius is deposited to the end surface on the output end side of the case body 2. As a result, the simulation results illustrated in FIGS. 3A to 3D were obtained. In FIGS. 3A to 3D, FIG. 3A is a perspective view of the case body 2, FIG. 3B is a bottom view thereof, FIG. 3C is a perspective view illustrating the light travel state, and FIG. 3D is bottom view illustrating the light travel state.

FIGS. 3A to 3D illustrate that ultraviolet rays travel in the body of the case body 2 to reach the end surface on the output end side of the case body 2.

Figure 4A:
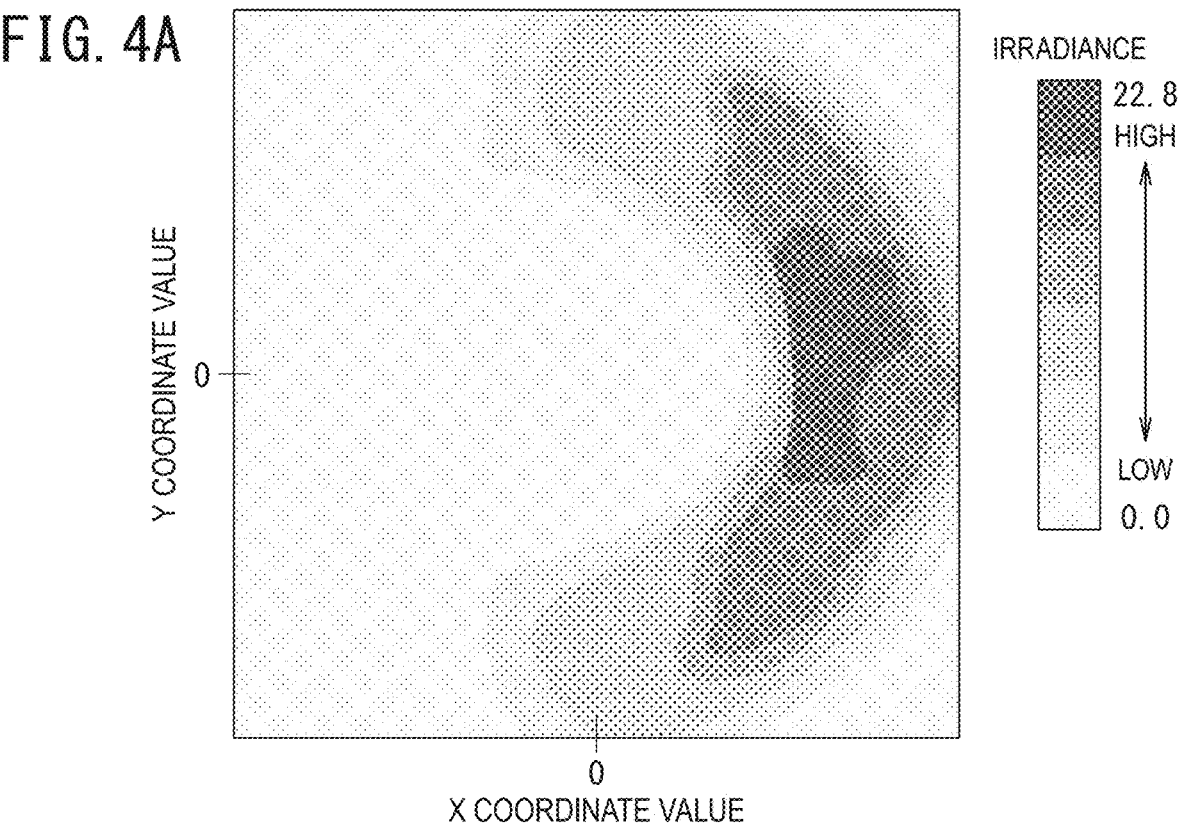
FIGS. 4A and 4B are examples of simulation results illustrating the irradiance on an end surface on the side of an output end of a case body.
Figure 4B:
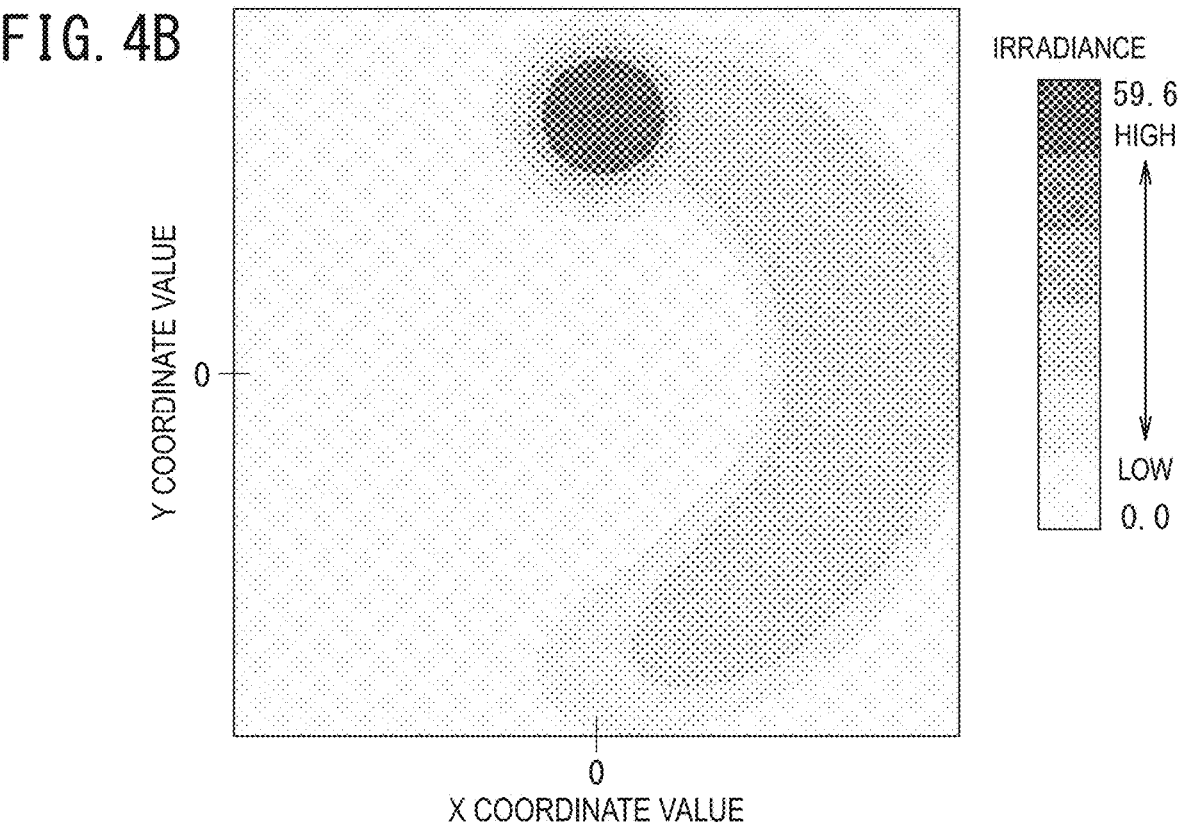

FIGS. 4A and 4B illustrate an example of the simulation results illustrating the irradiance of the ultraviolet rays on the end surface on the output end side of the case body 2. As illustrated in FIGS. 4A and 4B, it was able to be confirmed that the irradiance in the region where water droplets are deposited is the highest in the end surface on the output end side of the case body 2. In FIGS. 4A and 4B, FIG. 4A illustrates a case where a water droplet is not deposited in the end surface on the output end side of the case body 2 and FIG. 4B illustrates a case where a water droplet is deposited as illustrated in FIGS. 3A to 3D.

When no water droplets is deposited as illustrated in FIG. 4A, the total power of ultraviolet rays output from the end surface on the output end side of the case body 2 was 5.65 mW (28% to the output of the ultraviolet-ray irradiation portion 3) and the maximum illuminance was 22.8 mW/cm$^2$. On the other hand, when a water droplet is deposited as illustrated in FIG. 4B, the total power of ultraviolet rays output from the end surface on the output end side of the case body 2 was 7.48 mW (37% to the output of the ultraviolet-ray irradiation portion 3) and the maximum illuminance was 59.6 mW/cm$^2$. It was confirmed that the case where a water droplet is deposited is the same state as a state where light gathers to the water droplet and the maximum illuminance increased by 2.6 times.

Figure 5A:
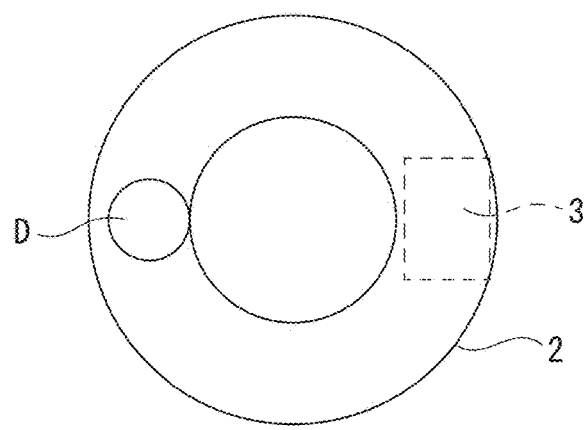
FIGS. 5A and 5B are the other examples of simulation results illustrating the irradiance on the end surface on the side of the output end of the case body.
Figure 5B:
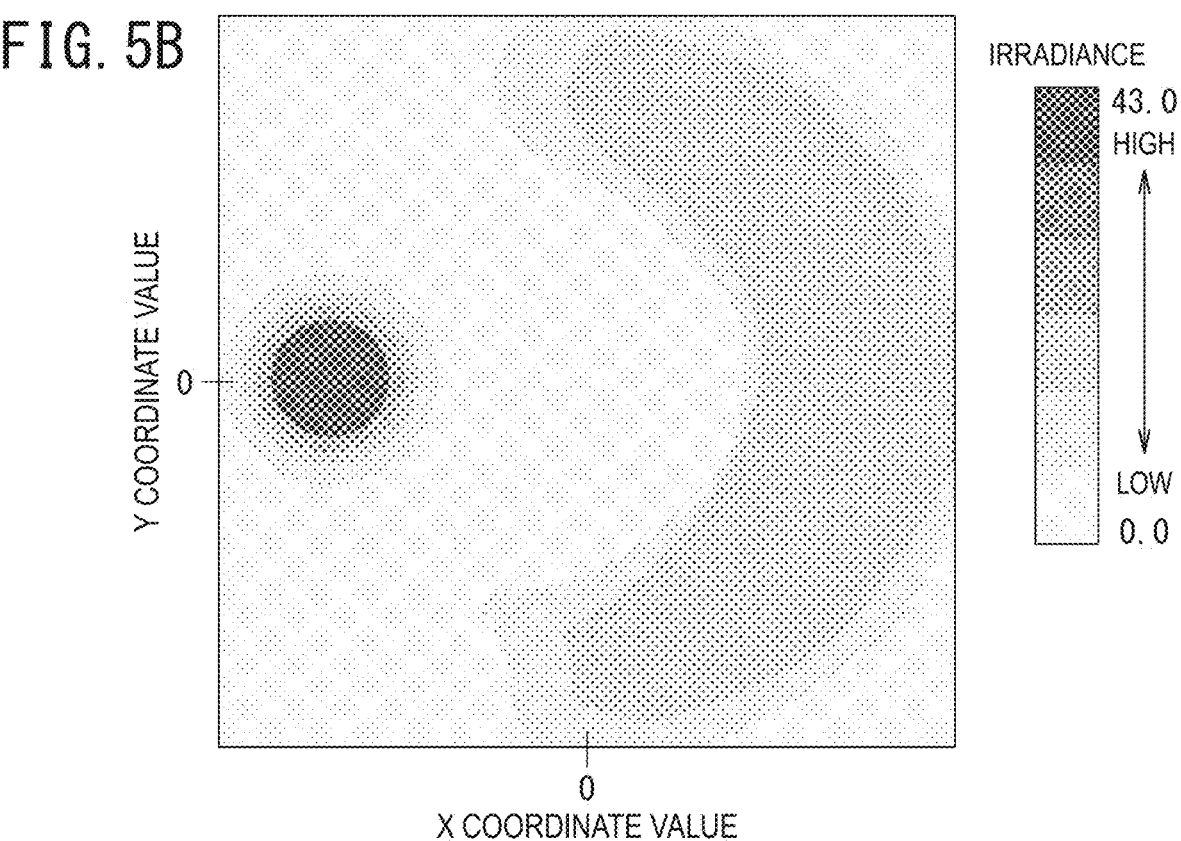

FIGS. 5A and 5B illustrate an example of simulation results illustrating the irradiance of ultraviolet rays in the end surface on the output end side when the water droplet D having a 1 mm radius that is deposited to the end surface on the output end side of the case body 2 is present at a position relatively distant from the ultraviolet-ray irradiation portion 3. When the water droplet D and the ultraviolet-ray irradiation portion 3 are disposed at a position where the water droplet D and the ultraviolet-ray irradiation portion 3 face each other across the flow passage as viewed in plan as illustrated in FIG. 5A, it was able to be confirmed that the irradiance in the region where the water droplet is deposited is the highest in the end surface on the output end side of the case body 2 as illustrated in FIG. 5B.

At this time, the total power of the ultraviolet rays output from the end surface on the output end portion side of the case body 2 was 7.2 mW (36% to the output of the ultraviolet-ray irradiation portion 3) and the maximum illuminance was 43 mW/cm$^2$. It was able to be confirmed from FIGS. 4A and 4B and FIGS. 5A and 5B that the irradiance is the highest in the region where the water droplet is deposited irrespective of the water droplet position.

When the illuminance increases, the ultraviolet ray irradiation time can be shortened or the irradiation output can be made low. Thus, efficient sterilization is enabled, and a load to the case body 2 and the like can be reduced, and thus the life of the sterilizer 1 can be increased.

Figure 6A:
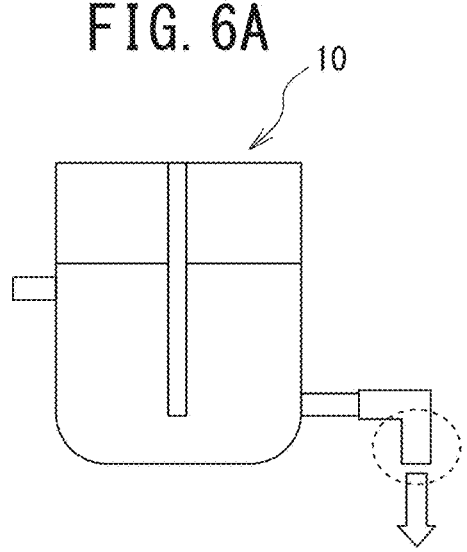
FIGS. 6A and 6B are schematic configuration diagrams illustrating an example of a water supply device having a sterilizer.
Figure 6B:
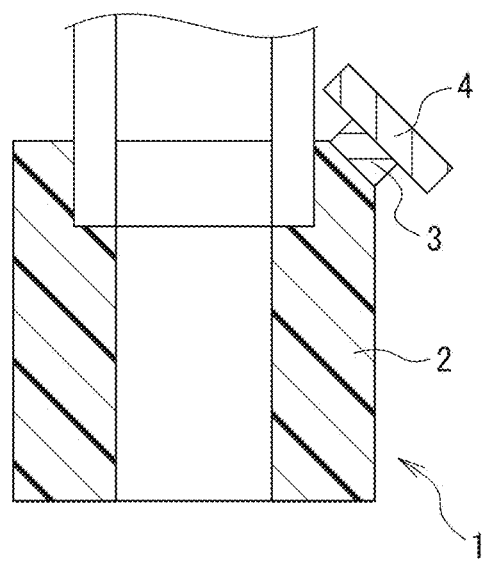

The sterilizer 1 may be configured so as to be separately attached to the supply port of the device for supplying a liquid or a solid or may be integrally formed with the supply port of a device for supplying a liquid or a solid 10 as illustrated in FIGS. 6A and 6B. FIG. 6B is an enlarged view of a supply port portion of FIG. 6A.

As the device for supplying a liquid or a solid 10, a server of liquid or ice, and the like are mentioned. The liquid refers to general substances having flowability, such as water, an aqueous solution, and an emulsion. Liquid for use in eating and drinking is preferable.

Examples of the liquid for use in eating and drinking include water, soft drinks, dairy-product drinks, milk, edible oil, and the like. Moreover, sherbet, jelly, soft ice cream, smoothie, cocoa/chocolate beverages and the like are also included.

The ice includes those obtained by freezing liquid for use in eating and drinking.

Examples of liquid other than the liquid for use in eating and drinking include water not for eating and drinking, such as ultrapure water, wash water, weak acidic water, and weak alkaline water, and industrial products, such as aqueous solutions of industrial raw materials and aqueous paints.

Examples of devices supplying the liquid or the ice include a water server, a tea dispenser, a beverage vending machine (one of a type of supplying beverages in a cup), an ice server, the other devices storing and supplying the liquid and the ice described above, and the like.

Modifications

Next, modifications are described.

Figure 7A:
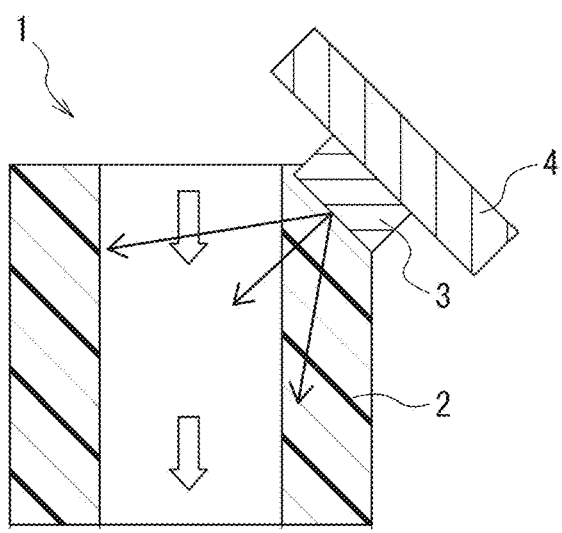
FIGS. 7A and 7B illustrate a modification of the sterilizer.
Figure 7B:
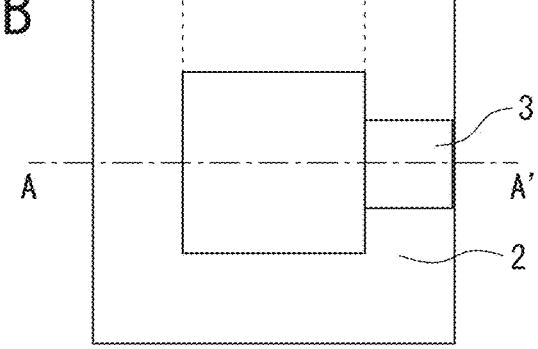

FIGS. 7A and 7B illustrate a case where the case body 2 is a hollow square pole in the sterilizer 1 illustrated in FIGS. 1A and 1B. The shape of the case body 2 may be a hollow cylinder or a hollow square pole and the cross sections of the inner surface and the outer surface do not necessarily need to be in agreement with each other. In brief, the shape of the sterilizer 1 may be any shape insofar as the inner peripheral surface can be attached in close contact with the outer periphery of a supply port of a device for supplying a liquid or a solid as the attachment destination of the sterilizer 1.

Figure 8A:
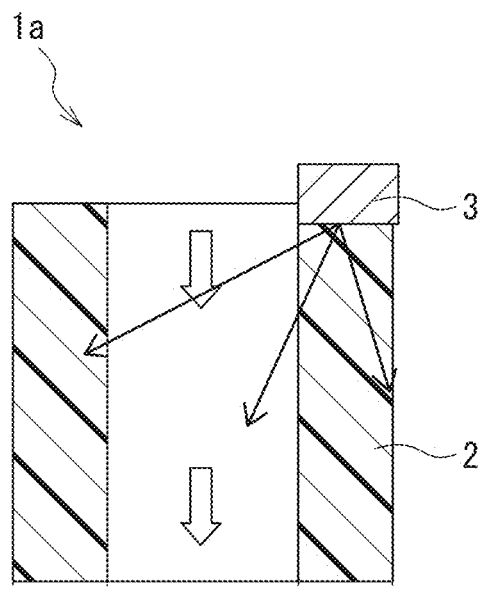
FIGS. 8A and 8B illustrate a modification of the sterilizer.
Figure 8B:
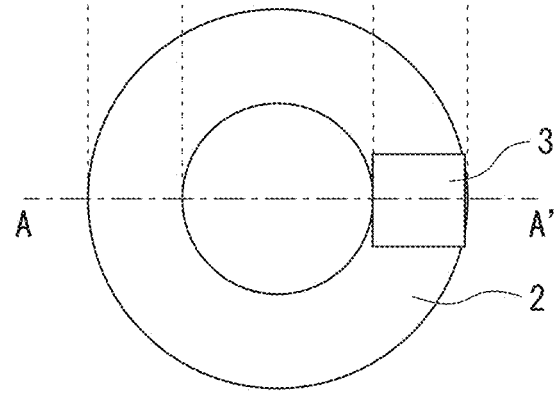

FIGS. 8A and 8B illustrate a sterilizer 1a different in the arrangement position of the ultraviolet-ray irradiation portion 3 in the sterilizer 1 illustrated in FIGS. 1A and 1B. In the sterilizer 1a, the ultraviolet-ray irradiation portion 3 is disposed in such a manner that the end surface on the attachment end side of the case body 2 and the light emission surface of the ultraviolet-ray irradiation portion 3 face each other. The ultraviolet-ray irradiation portion 3 may be disposed at any position insofar as the position is close to the end surface on the attachment end side of the case body 2, ultraviolet rays emitted from the ultraviolet-ray irradiation portion 3 reach the end surface on the output end side of the case body 2, and sufficient light quantity to sterilize water droplets deposited to the end surface on the output end side of the case body 2 or the vicinity of an end portion of the supply port of the case body 2 can be transmitted to an end portion on the output end side of the case body 2. The printed circuit board 4 is omitted in FIGS. 8A and 8B.

Herein, in FIGS. 7A and 7B and FIGS. 8A and 8B and the following FIGS. 9A and 9B and FIGS. 10A and 10B, FIGS. 7A, 8A, 9A, and 10A illustrate cross-sectional views of the A-A' line and FIGS. 7B, 8B, 9B, and 10B illustrate plan views.

Figure 9A:
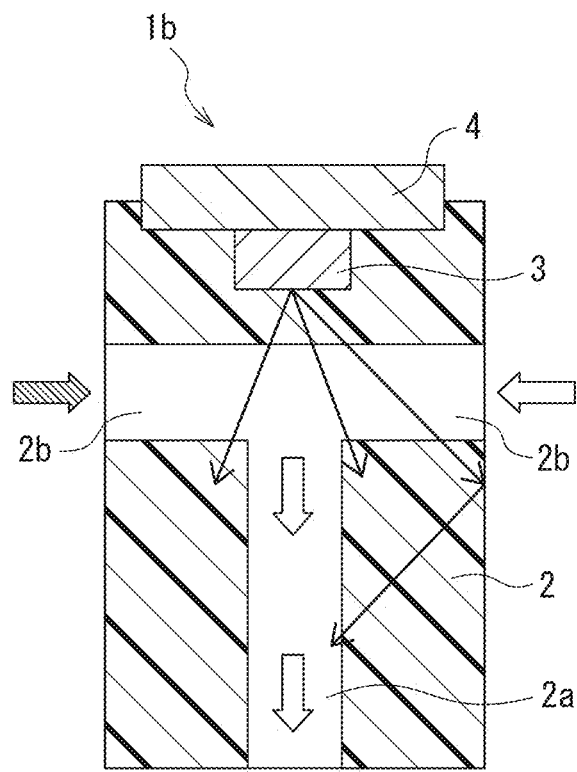
FIGS. 9A and 9B illustrate a modification of the sterilizer.
Figure 9B:
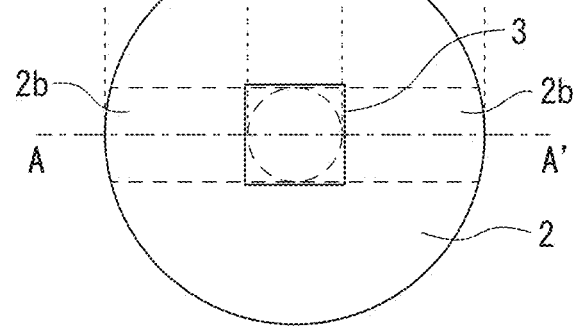

FIGS. 9A and 9B illustrate a sterilizer 1b configured to supply two kinds of liquid or ice from one supply port in the sterilizer 1 illustrated in FIGS. 1A and 1B. As illustrated in FIGS. 9A and 9B, the case body 2 of the sterilizer 1a is formed into a hollow cylinder to a position near an end portion on a side of the attachment end and further communicates with a pair of through-holes 2b penetrating the side surface of the case body 2 in an end portion of a hollow portion 2a on the attachment end side. The through-holes 2b are formed in such a manner as to face each other and end portions on the outer peripheral surface side of the case body 2 of the through-holes 2b serve as inlet ports of liquid, ice, or the like.

Moreover, as illustrated in FIGS. 9A and 9B, the ultraviolet-ray irradiation portion 3 is disposed near a central portion of the end surface as viewed in plan on the end surface on the attachment end side of the case body 2. Due to the fact that the ultraviolet-ray irradiation portion 3 is disposed near the central portion as described above, ultraviolet rays travel in the longitudinal direction of the case body 2 while being diffused from the vicinity of the central portion to the entire periphery of an edge portion of the case body 2. Therefore, the ultraviolet rays substantially uniformly travel in the body in the longitudinal direction over the entire periphery of the case body 2, and thus sterilization can be equally performed. The arrangement position of the ultraviolet-ray irradiation portion 3 is not limited thereto and the ultraviolet-ray irradiation portion 3 may be disposed at a position closer to the outer periphery of the end surface on the attachment end side of the case body 2 or may be disposed to be inclined on a corner portion on the attachment end side of the case body 2 in the same manner as the sterilizer 1 illustrated in FIGS. 1A and 1B and may be disposed at any position where ultraviolet rays sufficient to perform sterilization can reach the end portion on the output end side of the case body 2.

Figure 10A:
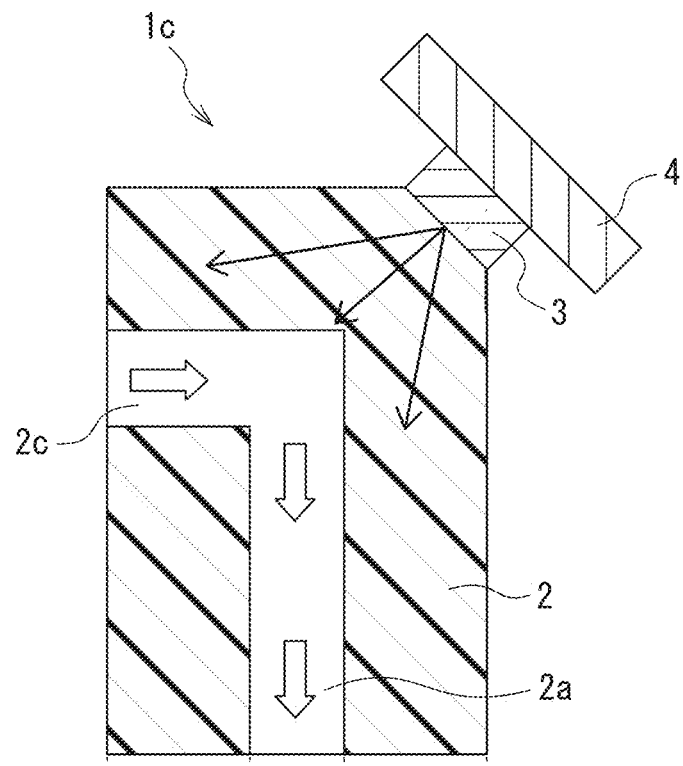
FIGS. 10A and 10B illustrate a modification of the sterilizer.
Figure 10B:
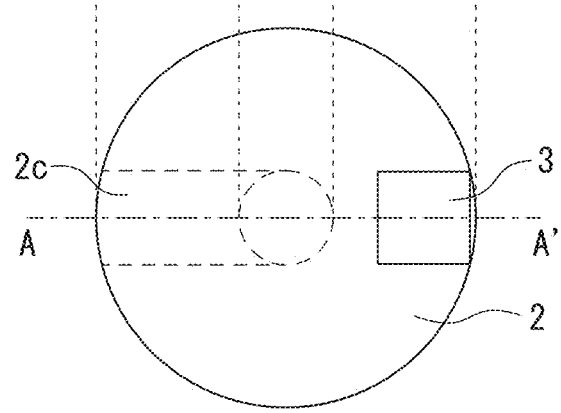

FIGS. 10A and 10B illustrate a sterilizer 1c configured to input liquid or ice from the side surface and output the same from the end surface on a side of an output end in the sterilizer 1 illustrated in FIGS. 1A and 1B. As illustrated in FIGS. 10A and 10B, the case body 2 of the sterilizer 1c is formed into a hollow cylinder to a position near an end portion on the attachment end side and further communicates with a through-hole 2c penetrating the side surface of the case body 2 in an end portion of the hollow portion 2a on the attachment end side.

Moreover, as illustrated in FIG. 10B, the ultraviolet-ray irradiation portion 3 is disposed on a corner portion on the attachment end side of the case body 2 and is disposed in such a manner that the through-hole 2c and the ultraviolet-ray irradiation portion 3 are located on the same straight line as viewed in plan. When disposed as described above, the optical path length to the end surface on the output end side of the case body 2 is shorter, and therefore the arrangement is preferable. The arrangement position of the ultraviolet-ray irradiation portion 3 is not limited thereto and may be disposed at a position closer to the outer periphery of the end surface on the attachment end side of the case body 2 or may be disposed in such a manner that the end surface on the attachment end side of the case body 2 and the emission surface of the ultraviolet-ray irradiation portion 3 face each other in the same manner as the sterilizer 1a illustrated in FIGS. 8A and 8B and may be disposed at any position where ultraviolet rays sufficient to perform sterilization can reach the end portion on the output end side of the case body 2.

Figure 11A:
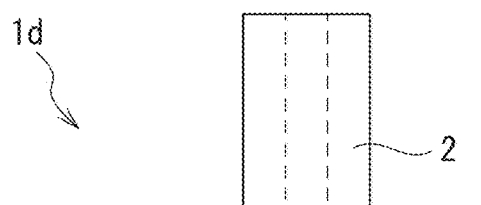
FIGS. 11A and 11B illustrate a modification of the sterilizer.
Figure 11B:
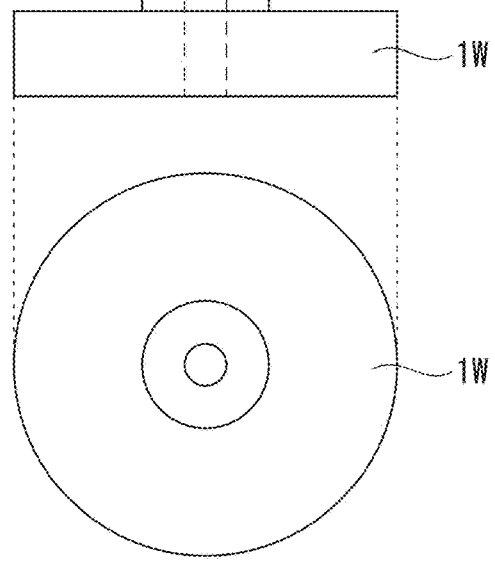
Figure 12A:
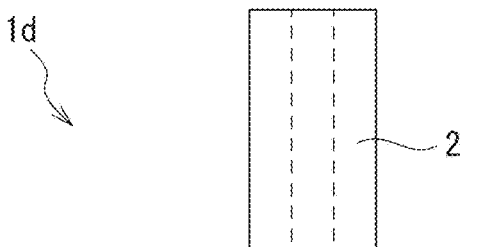
FIGS. 12A and 12B illustrate a modification of the sterilizer.
Figure 12B:
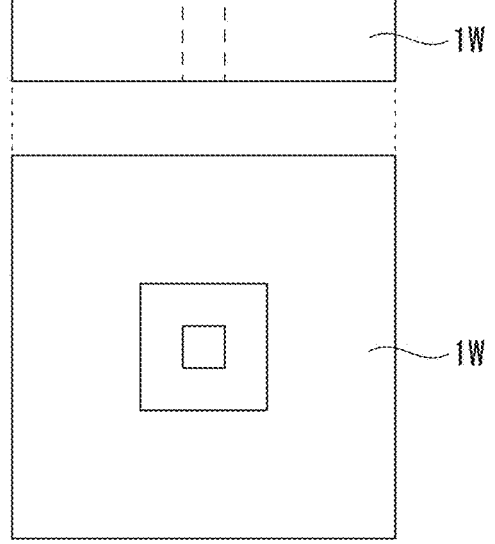

FIGS. 11A and 11B and FIGS. 12A and 12B illustrate a sterilizer 1d having an enlarged portion 1W on the end surface on a side of the output end in the sterilizer 1 illustrated in FIGS. 1A and 1B. FIGS. 11A and 11B illustrate a case where the case body 2 is a hollow cylinder and FIGS. 12A and 12B illustrate a case where the case body 2 is a hollow square pole. In FIGS. 11A and 11B and FIGS. 12A and 12B, FIGS. 11A and 12A are side views and FIGS. 11B and 12B are plan views. In the case body 2, an end portion on the output end side is formed into a flange shape and the flange portion forms the enlarged portion 1W. As illustrated in FIGS. 11A and 11B and FIGS. 12A and 12B, when the enlarged portion 1W is provided in the end portion on the output end side, most of droplets of drinking water or the like scattering and rebounding from a container receiving the drinking water or the like to be supplied through the sterilizer 1 can be received on the end surface on the output end side including the enlarged portion 1W, and thus scattering to the other places, such as the outer periphery of the case body 2, can be prevented.

Figure 13A:
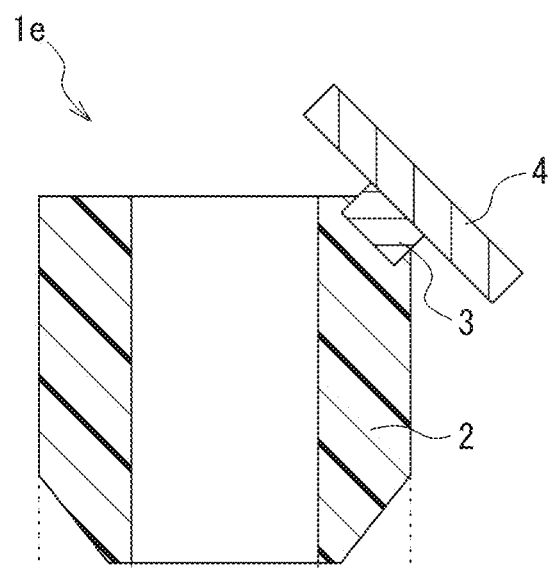
FIGS. 13A and 13B illustrate a modification of the sterilizer.
Figure 13B:
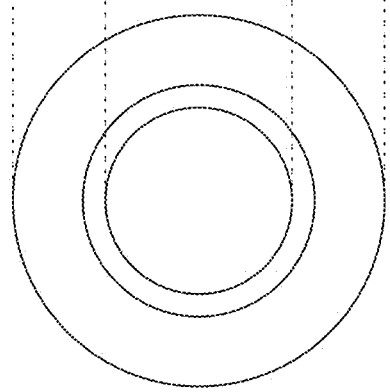

FIGS. 13A and 13B illustrate a sterilizer 1e in which the output end side of the case body 2 has a tapered shape in which the width is narrowed as it approaches an end portion as viewed from the side surface in the sterilizer 1 illustrated in FIGS. 1A and 1B. When an end portion on the output end side has the tapered shape, drinking water or the like scattering and rebounding from a container receiving the drinking water or the like to be supplied through the sterilizer 1 can be received by the tapered portion, and then can be collected to the end portion on the output end side of the case body 2 through an inclined surface thereof, and thus ultraviolet rays can be sufficiently emitted to the collected drinking water or the like.

Figure 14:
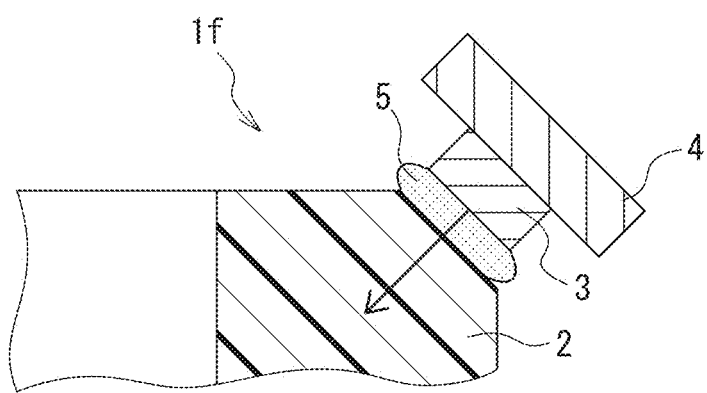
FIG. 14 illustrates a modification of the sterilizer.

A sterilizer 1f illustrated in FIG. 14 is configured so that a filler 5 is interposed between the ultraviolet-ray irradiation portion 3 and the case body 2 when the ultraviolet-ray irradiation portion 3 is attached to the case body 2 in the sterilizer 1 illustrated in FIGS. 1A and 1B. FIG. 14 illustrates only a principal portion.

Figure 15:
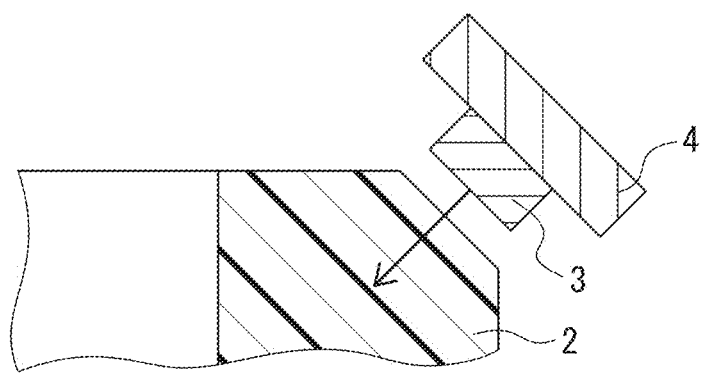
FIG. 15 is an explanatory view for explaining an operation of the sterilizers in the modifications.

More specifically, when ultraviolet rays are made incident from the ultraviolet-ray irradiation portion 3 to the case body 2 containing a translucent material, when an air interface is present between the ultraviolet-ray irradiation portion 3 and the body the case body 2 as illustrated in FIG. 15, interface reflection arises on the air interface, and thus the amount of the ultraviolet rays diffused into the body of the case body 2 correspondingly decreases. As a result, the amount of the ultraviolet rays transmitted to an end portion on the output end side of the case body 2 decreases. Specifically, when a material on the side contacting the air interface of the ultraviolet-ray irradiation portion 3 is quartz (Optical refractive index n=1.5) and a material of the case body 2 is silicone resin (Optical refractive index n=1.41), the refractive index changes to 1 from 1.5, and then changes to 1.41 from 1 twice even when only straight light is supposed, and, at that time, high interface reflection arises, and therefore the amount of ultraviolet rays decreases by 6.78%. Therefore, by bringing the case body 2 and the irradiation surface of the ultraviolet-ray irradiation portion 3 into direct contact with each other as illustrated in FIGS. 1A and 1B or disposing the filler 5 between the case body 2 and the irradiation surface of the ultraviolet-ray irradiation portion 3 as illustrated in FIGS. 14A and 14B, the formation of the air interface between the case body 2 and the irradiation surface of the ultraviolet-ray irradiation portion 3 is avoided, whereby the interface reflection based on a large refractive index change on the air interface of the ultraviolet rays can be prevented, and, as a result, a reduction in the ultraviolet rays to be transmitted to the end portion on the output end side of the case body 2 can be avoided.

The filler 5 is formed of a material having an optical refractive index closer to the optical refractive index to ultraviolet rays of a member of the ultraviolet-ray irradiation portion 3, i.e., a member configuring a portion where ultraviolet rays to be emitted from the ultraviolet-ray irradiation portion 3 are emitted, and then radiated to the filler 5 through a portion contacting the filler 5 of the ultraviolet-ray irradiation portion 3 of the portion, and the optical refractive index to ultraviolet rays of a member configuring the case body 2. For example, when a material of the case body 2 is silicone resin (Optical refractive index n=1.41) or quartz (Optical refractive index n=1.5) and a material of the member of the ultraviolet-ray irradiation portion 3 is quartz (Optical refractive index n=1.5), silicone resin (Optical refractive index n=1.41), fluororesin (Optical refractive index n=1.35) or the like is applicable as the filler 5, for example.

Specifically, when fluororesin (Optical refractive index n=1.35) is used as the filler 5 in a case where a material on a side contacting the filler 5 of the ultraviolet-ray irradiation portion 3 is quartz (Optical refractive index n=1.5) and a material of the case body 2 is silicone resin (Optical refractive index n=1.41), the refractive index changes to 1.35 from 1.5, and then changes to 1.41 from 1.35 when only straight light is supposed, and therefore two interface reflections arise but the refractive index change is small, and therefore the amount of ultraviolet rays decreases by only 0.32%.

FIG. 14 illustrates the case where the filler 5 is interposed between the surface of the ultraviolet-ray irradiation portion 3 and the surface of the case body 2. However, a state in which the side surface of the ultraviolet-ray irradiation portion 3 is embedded in the filler 5, for example, may be acceptable. Also in this case, ultraviolet rays are directly emitted from the ultraviolet-ray irradiation portion 3 to the filler 5 not through an air layer or the like, and therefore attenuation of the ultraviolet rays when irradiation light of the ultraviolet-ray irradiation portion 3 is emitted to the case body 2 can be suppressed. On the other hand, when the ultraviolet-ray irradiation portion 3 is stored in a package, an air layer is present in the package, and therefore there is a possibility that ultraviolet ray to be emitted from the package somewhat decreases as compared with a case where the irradiation surface of the ultraviolet-ray irradiation portion 3 directly contacts the filler 5. However, by bringing the light irradiation surface of the package and the filler 5 into a direct contact with each other, the decrease of the ultraviolet ray between the package and the filler 5 can be suppressed.

As described above, the embodiments of the present invention are described but the above embodiments describe examples of a device or a method for crystalizing the technical idea of the present invention and the technical idea of the present invention does not specify materials, shapes, structures, arrangement, and the like of constituent components. The technical idea of the present invention can be variously altered in the technical scope specified by Claims.

DESCRIPTION OF REFERENCE NUMERALS 1, 1a to 1f sterilizer
2 case body
3 ultraviolet-ray irradiation portion
5 filler
10 device for supplying a liquid or a solid

What is claimed is:
1. A sterilizer comprising:
a case body composed of a member having an ultraviolet-ray transmission property, and including a discharge passage formed inside the case body; and
a light source, disposed (i) on a central portion of an end surface on an attachment end side of the case body or (ii) on a corner portion on the attachment end side of the case body, the light source irradiating a predetermined portion of the member with ultraviolet rays, wherein
the ultraviolet rays emitted from the light source travel in a body of the case body and the ultraviolet rays are radiated at least from an end surface on a side of a discharge port of the case body, a filler is present between the case body and the light source, wherein a refractive index of the filler is different from a refractive index of the case body, and the light source is disposed in contact with the filler, wherein the ultraviolet rays are emitted to the case body through the filler.

2. The sterilizer according to claim 1, wherein the light source is an ultraviolet-ray emitting diode emitting ultraviolet rays with a center wavelength of 230 nm or more and 300 nm or less.

3. The sterilizer according to claim 1, wherein the ultraviolet rays are emitted to a body to be irradiated deposited to the end surface on the side of the discharge port.

4. The sterilizer according to claim 1, wherein the case body is composed of a material transmitting 30%/cm or more of ultraviolet rays with a center wavelength of 230 nm or more and 300 nm or less.

5. The sterilizer according to claim 1, wherein when an optical refractive index of a light emission portion of the light source is set to Nd, an optical refractive index of the case body is 1.29 or more and the Nd or less.

6. The sterilizer according to claim 1, wherein the case body contains at least one of crystal, quartz, silicone resin, fluororesin, and polyolefin.

7. The sterilizer according to claim 1, wherein the filler contains either silicone resin or fluororesin.

8. The sterilizer according to claim 1, wherein the case body is partially covered with an ultraviolet-ray reflecting substance.

9. The sterilizer according to claim 8, wherein the ultraviolet-ray reflecting substance contains at least one of aluminum, gold, silver, copper, and a platinum group element including platinum, or an alloy containing thereof.

10. The sterilizer according to claim 1, wherein the case body has a hollow columnar shape, the discharge port of the discharge passage is provided in one end surface of the case body, and the light source is provided at a position except the end surface in which the discharge port is provided in the case body.

11. The sterilizer according to claim 1, wherein an end portion on a side in which the discharge port is provided in the case body is formed into a flange shape.

12. The sterilizer according to claim 1, wherein a side surface of the case body has a tapered portion in which a width is narrowed toward the end surface in which the discharge port is provided as viewed from the side surface.

13. The sterilizer according to claim 1, wherein food and drink pass through the discharge passage.

14. A device for supplying liquid or a solid obtained by freezing liquid, comprising the sterilizer according to claim 1 in a supply port.

15. A sterilization method comprising:

disposing the sterilizer according to claim 1 in a supply port of a device for supplying liquid or a solid obtained by freezing liquid, and covering the supply port with the sterilizer to suppress proliferation of bacteria in the supply port.

16. The sterilizer according to claim 2, wherein the ultraviolet rays are emitted to a body to be irradiated deposited to the end surface on the side of the discharge port.

17. The sterilizer according to claim 2, wherein the case body is composed of a material transmitting 30%/cm or more of ultraviolet rays with a center wavelength of 230 nm or more and 300 nm or less.

18. The sterilizer according to claim 1, wherein the light source is disposed on the central portion of the end surface on the attachment end side of the case body.

19. The sterilizer according to claim 1, wherein the light source is disposed on the corner portion on the attachment end side of the case body.

* * * * *